United States Patent [19]

Takekoshi et al.

[11] Patent Number: 4,808,696

[45] Date of Patent: Feb. 28, 1989

[54] METHOD FOR MAKING ORGANOBIS(THIOETHER)S, AND PRODUCTS OBTAINED THEREFROM

[75] Inventors: Tohru Takekoshi, Scotia; Patricia P. Anderson, Albany; Thomas L. Evans, Clifton Park, all of N.Y.

[73] Assignee: General Electric Company, Schenectady, N.Y.

[21] Appl. No.: 56,511

[22] Filed: Jun. 1, 1987

[51] Int. Cl.$^4$ ............................................. C08G 69/26
[52] U.S. Cl. .................................. 528/353; 528/352; 528/229; 528/188
[58] Field of Search ................ 528/353, 352, 229, 188

[56] References Cited

U.S. PATENT DOCUMENTS 3,933,749 1/1976 Williams .......................... 260/47 CP
3,933,862 1/1976 Williams .......................... 260/346.3

OTHER PUBLICATIONS

Chem Abstract 102:955375 Mercaptophthalimide derivatives, Evans, Thomas, Lane (General Electric Co.).

Primary Examiner—John Kight
Assistant Examiner—M. L. Moore
Attorney, Agent, or Firm—William A. Teoli; James C. Davis, Jr.; James Magee, Jr.

[57] ABSTRACT

A method is provided for making organobis(thioether)s which include bis(thioetherimide)s and bis(thioetheranhydride)s. There is also provided alkylene bis(thioetherimide)s and the corresponding dianhydrides thereof which can be used to make crystalline polyimides.

10 Claims, No Drawings

METHOD FOR MAKING ORGANOBIS(THIOETHER)S, AND PRODUCTS OBTAINED THEREFROM

BACKGROUND OF THE INVENTION

The present invention relates in part to a method for making organobis(thioetherimide)s having the formula,

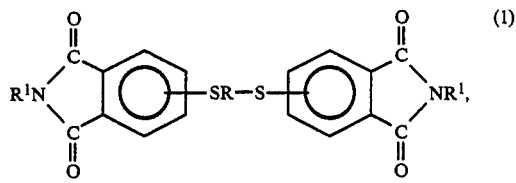

where R is a $C_{(2-20)}$ divalent organo radical, and $R^1$ is a $C_{(1-14)}$ monovalent organo radical. The organo bis(thioetherimide)s of formula (1) can be hydrolyzed to the corresponding anhydrides thereafter copolymerized with aromatic diamines to make polyimides.

Prior to the present invention, as shown by F. J. Williams, U.S. Pat. No. 3,933,862, and U.S. Pat. No. 3,933,749, aromatic bisimides and dianhydrides were made by displacing nitro radicals on nitrophthalimides with bisthiophenols. Bis-thiophenols, however, are not readily accessible, since they have to be synthesized in a multistep manner.

The present invention is based on the discovery that N-substituted phthalimidothiolate can react with alkylene dihalides, or activated dihalo aromatic compounds to provide the organobis(thioetherimide)s of formula (1), as shown by the following equation,

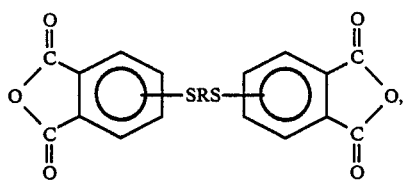

where R and $R^1$ are as previously defined, and X is a halogen radical.

STATEMENT OF THE INVENTION

One aspect of the present invention is directed to a method for making organo bis(thioetheranhydride) of the formula,

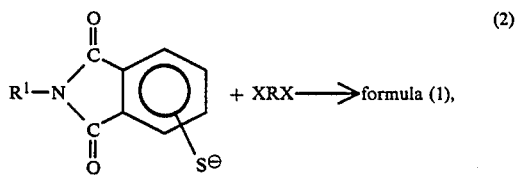

which comprises
(1) effecting the hydrolysis of organo bis(thioetherimide) of formula (1), and
(2) thereafter cyclodehydrating the resulting tetraacid,
where R is as previously defined.

Radicals included within R of formulas (1) and (3) are, for example, divalent alkylene radicals such as methylene, ethylene, trimethylene, tetramethylene, pentamethylene, hexamethylene; arylene radicals such as phenylene, xylylene, tolylene, naphthylene, biphenylene, anthralene, and divalent radicals of the formula,

where $X^1$ is a member selected from the class consisting of $-SO_2-$, $-S-$, and

and p is an integer from 1 to 4.

Radicals included within $R^1$ are, for example, $C_{(1-8)}$ alkyl radicals such as methyl, ethyl, propyl, butyl, pentyl, hexyl, and $C_{(6-14)}$ aryl radicals such as phenyl, xylyl, tolyl.

In a further aspect of the present invention, there is provided organobis(thioether)s of the formula,

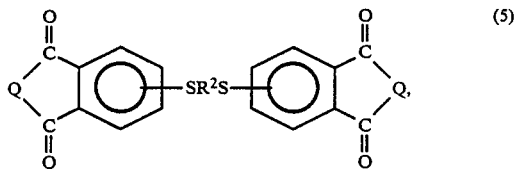

where $R^2$ is a $C_{(1-10)}$ divalent alkylene radical, and Q is a member selected from the class consisting of $-O-$ and $=NR^1$, where $R^1$ is as previously defined.

In an additional aspect of the present invention, there is provided highly crystalline polyimides having chemically combined units of formula (10) below, which can be made by effecting reaction between alkylene bis(-thioether-anhydride)s of the formula,

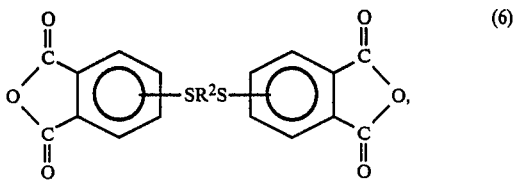

and aromatic diamines of the formula, $$NH_2R^3NH_2, \qquad (7)$$

where $R^2$ is as previously defined, and $R^3$ is a divalent $C_{(6-27)}$ aromatic hydrocarbon radical or a divalent $C_{(6-27)}$ aromatic hydrocarbon radical substituted with radicals inert during intercondensation.

A significant aspect of the present invention is the generation of N-substituted phthalimidothiolate of the formula, as shown in equation (2) which can be achieved by the nucleophilic displacement of thiobisphthalimides with sodium sulfide in a dipolar aprotic solvent as shown by the following equation,

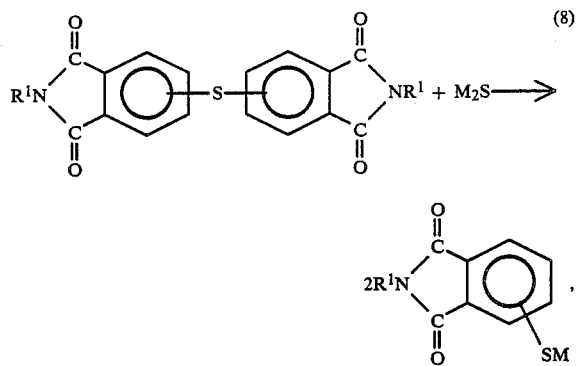

where $R^1$ is as previously defined, and M is an alkali metal ion, for example, sodium or potassium.

Another procedure for making the N-substituted phthalimidothiolate of equation (8) is by effecting reaction between an N-substituted halophthalimide and sodium sulfide as shown by the following equation,

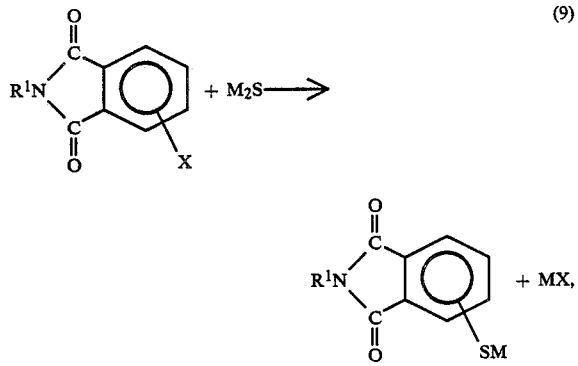

where $R^1$, and M are as previously defined.

Aromatic diamines which are included within formula (7) are, for example,
m-phenylenediamine;
p-phenylenediamine;
4,4'-diaminodiphenylpropane,
4,4-diaminodiphenylmethane; benzidine;
4,4'-diaminodiphenyl sulfide;
4,4'-diaminodiphenylsulfone;
4,4'-diaminodiphenyl ether;
1,5'-diaminonaphthalene,
3,3'-dimethylbenzidine;
3,3'-dimethoxybenzidine;
2,4-bis($\beta$-amino-t-butyl)toluene;
bis(p-$\beta$-amino-t-butylphenyl)ether;
bis(p-$\beta$-methyl-o-aminopentyl)benzene;
1,3'-diamino-4-isopropylbenzene;
1,2-bis(3-aminopropoxy)ethane;
m-xylylenediamine;
p-xylylenediamine;
2,4-diaminotoluene;
2,6-diaminotoluene;
1,3-bis(4-aminophenoxy)benzene;
1,4-bis(4-aminophenoxy)benzene;
4,4'-bis(4-aminophenoxy)diphenylpropane;
4,4'-bis(4-aminophenoxy)diphenyl ether; and
4,4'-bis(4-aminophenoxy)diphenyl sulfide.

In making the bis(thioetherimide)s of formula (1), the temperature required for the reaction of the organic dihalide and the N-substituted phthalimido dithiolate as shown by equation (2) can vary widely depending upon the reactivity of the organic dihalide. For example, alkylene dihalides are found to be the most reactive and react at amibient temperatures very rapidly. Aromatic dihalides require 100° C. or higher. Bis(thiophthalimido)alkanes form readily and are found to be high melting crystalline compounds. The bisimides can be readily converted to the corresponding tetra acids by the action of alkali hydroxide, such as aqueous sodium hydroxide followed by acidification with a mineral acid, for example aqueous hydrochloric acid and cyclodehydrated with a dehydrating agent, such as acetic anhydride, to produce the corresponding dianhydride. Highly crystalline polyimides consisting essentially of chemically combined units of the formula,

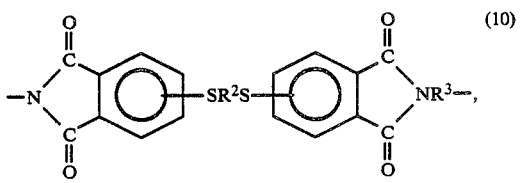

can be made when the alkylene bis(thioetheranhydride) of formula (6) are intercondensed with aromatic diamine of formula (7) where $R^2$ and $R^3$ are as previously defined.

The following examples are given by way of illustration and not by way of limitation. All parts are by weight.

EXAMPLE 1

A mixture of 2.476 grams (0.03172 mole) of anhydrous sodium sulfide, 11.178 grams (0.03172 mole) of bis(N-methyl-4-phthalimido)sulfide and 30 ml of N-methylpyrrolidone was stirred and heated under a nitrogen atmosphere at 95° C. for 6½ hours. Reaction mixture was cooled to 40° C. and 5.959 grams (0.03172 mole) of 1,2-dibromoethane was added. An exotherm and massive precipitation of solids occurred. Additional N-methylpyrrolidone was added and the mixture was stirred overnight at room temperature. Reaction mixture was then added into water to produce a solid precipitate which was filtered, washed with water and methanol and dried. The crude product was recrystallized from N,N-dimethylacetamide to provide a yield of 92.5%. Based on method of preparation, the product was 1,2-bis(N-methylphthalimido-4-thio)ethane. Its identity was further confirmed by IR and $^{13}$C nmr spectroscopy.

A mixture of 33 ml of water and 7.32 grams (0.183 mole) of sodium hydroxide and 10.48 grams (0.0254 mole) of the above bisimide was stirred under nitrogen and heated to reflux. Methylamine was continuously distilled off and water was continuously added to the mixture. After 55 hours of heating, the reaction mixture was cooled and filtered. The filtrate was poured into 250 ml of a 3.3% aqueous hydrochloric acid. The precipitated solid was filtered, washed with water and dried. There was obtained 92.3% yield of a yellow crystalline solid having a melting point of 191°-194° C. Based on method of preparation and $^{13}$C nmr, the product was 1,2-bis(3,4-dicarboxyphenylthio)ethane.

A mixture consisting of 9.90 grams (0.0234 mole) of 1,2-bis(3,4-dicarboxyphenylthio)ethane, 6.77 grams (0.0669 mole) of acetic anhydride, and 30 ml of acetic acid was heated and stirred under nitrogen at 120° C. for 2 hours. Thick yellow slurry was obtained which was cooled and filtered. There was obtained 96.4% yield of a crystalline solid which was recrystallized from ortho-dichlorobenzene containing a few drops of acetic anhydride. There was obtained 75.7% yield of product having a melting point of 225°-226.5° C. Based on method of preparation, the product was 1,2-bis(3,4-dicarboxyphenylthio)ethane dianhydride. Its identity was further confirmed by $^{13}C$ nmr and IR spectroscopy.

EXAMPLE 2

In accordance with the procedure of Example 1, sodium N-methylphthalimidothiolate was prepared from 2.970 grams (0.03804 mole) of sodium sulfide, 13.405 grams (0.03804 mole) of bis(N-methylphthalimido)sulfide, and 40 ml of N-methylpyrrolidone. The solution was cooled and 10.924 grams (0.03804 mole) of 4,4'-dichlorodiphenylsulfone was added. The mixture was heated at 110° C. for 6 hours under nitrogen atmosphere. The resulting solution was cooled to room temperature and poured into 300 ml of water. There was obtained a solid precipitate which was filtered, washed with methanol and dried. The crude product (yield 93.6%) was recrystallized from toluene, using activated carbon. There was obtained a yield of 62% of white crystal having a melting point of 187°-191° C. Based on method of preparation, the product was 4,4'-bis(N-methylphthalimido-4-thio)diphenylsulfone. The same procedure was repeated with additional organic dihalides to produce the corresponding 4,4'-bis(N-methylphthalimido-4-thio) organic compounds which were hydrolyzed to the corresponding tetra acids and thereafter cyclodehydrated to the corresponding dianhydrides. The Table I shows the melting points and the crude yields of the bisimides obtained following the same procedure:

TABLE I
Bis(thioetherimide)s

| —R— | mp. (°C.) | Yield (%) |
|---|---|---|
| —(CH$_2$)$_2$— | 272–274.5 | 92.7 |
| —(CH$_2$)$_3$— | 142–143 | 71.7 |
| —(CH$_2$)$_4$— | 224–225 | 79.6 |
| —(CH$_2$)$_6$— | 218.5–220 | 79.3 |
| —(CH$_2$)$_{10}$— | 194–195.5 | 80.9 |
| —C$_6$H$_4$—SO$_2$—C$_6$H$_4$— | 187–191 | 93.6 |
| —C$_6$H$_4$—C(O)—C$_6$H$_4$— | 183–190 | 70.5 |

TABLE I-continued
Bis(thioetherimide)s

| —R— | mp. (°C.) | Yield (%) |
|---|---|---|
| —(C$_6$H$_4$—S—C$_6$H$_4$)$_2$— | 159–161 | 97.1 |

The above bisimides were hydrolyzed and cyclodehydrated to produce the corresponding dianhydrides which are shown in Table II.

TABLE II
Bis(thioetheranhydride)s

| No. | —R— | m.p. (°C.) | Yield (%) |
|---|---|---|---|
| 1 | —(CH$_2$)$_2$— | 225–226.5 | 96.4 |
| 2 | —(CH$_2$)$_6$— | 191–192.5 | 96.4 |
| 3 | —(CH$_2$)$_4$— | 248–250 | 97.3 |
| 4 | —(CH$_2$)$_6$— | 194–196 | 67.0 |
| 5 | —(CH$_2$)$_{10}$— | 164–170 | 88.2 |
| 6 | —C$_6$H$_4$—SO$_2$—C$_6$H$_4$— | 227–231 | 82.7 |
| 7 | —(C$_6$H$_4$—S—C$_6$H$_4$)$_2$— | 201–202 | 93.6 |

EXAMPLE 3

A mixture of 3.575 grams (13.88 millimoles) of N-phenyl-4-chlorophthalimide, 1.083 grams (13.88 millimoles) of anhydrous sodium sulfide, and 12 ml of N-methylpyrrolidone was heated under a nitrogen atmosphere with stirring at 65°-75° C. for 10 hours. Based on HPLC analysis, the N-phenyl-4-chlorophthalimide was completely converted to the corresponding N-substituted phthalimidothiolate.

The solution was cooled to room temperature and 1.303 grams (6.938 millimoles) of 1,2-dibromoethane was added. The reaction mixture was further stirred at room temperature for 15 hours and then poured into water. There was obtained a white precipitate which was filtered, washed with water, and then with methanol and dried. There was obtained 2.65 grams (71.2%) yield of product. Melting point of the product was 264°-267° C. Based on method of preparation and its IR and $^{13}C$ NMR spectra, the product was 1,2-bis(N-phenylphthalimide-4-thio)ethane.

EXAMPLE 4

Equal molar amounts of dianhydrides listed in Table II and various aromatic diamines were intercondensed at temperatures in the range of 25° C. to 300° C. in the presence of N,N-dimethylacetamide. The results are summarized in Table III which includes diamines used, the polymer melting temperatures ($T_m$) and the glass transition temperatures ($T_g$).

TABLE III
Polyimides Prepared From Bis(thioetheranhydride)s

| Bis(thioether-anhydride)s | Diamines | $T_g$ (°C.) | $T_m$ (°C.) |
| --- | --- | --- | --- |
| 1 | m-phenylenediamine | 263 | 340 |
| 1 | 4,4'-oxydianiline | 168 | 285 |
| 1 | 1,3-bis(4-aminophenoxy)benzene | 203 | 248 |
| 1 | 4,4-bis(4-aminophenoxy)-diphenylsulfide | 160 | 259 |
| 2 | same | 145 | 224 |
| 2 | p-phenylenediamine | — | 401 |
| 3 | m-phenylenediamine | 158 | 251 |
| 3 | 4,4'-oxydianiline | 136 | 269 |

In addition to the above properties shown in Table III, the polyimides were found to be extremely resistant to aggressive solvents such as chlorinated hydrocarbons and dipolar solvents. These polyimides can be used as injection moldable thermoplastics and are useful in making composites with carbon fibers or glass fibers.

Although the above examples are directed to only a few of the very many variables which can be used in the practice of the method of the present invention, it should be understood that the present invention is directed to a much broader variety of organobis(thioetheranhydride)s or corresponding bisimides and polyimides made therefrom.

What is claimed and sought to be protected by Letters Patent of the United States is as follows:

1. Crystalline aromatic polyimides having alkylene disulfide groups comprising chemically combined units of the formula,

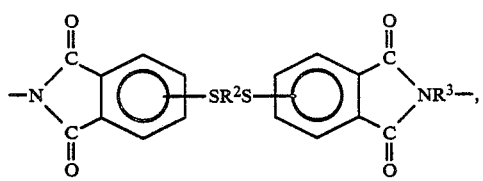

where $R^2$ is a $C_{(1-10)}$ divalent alkylene radical, and $R^3$ is a divalent $C_{(6-27)}$ aromatic hydrocarbon radical, or a divalent $C_{(6-27)}$ aromatic hydrocarbon radical substituted with radicals neutral during intercondensation.

2. Polyimides in accordance with claim 1, where $R^2$ is dimethylene.

3. Polyimides in accordance with claim 1, where $R^3$ is phenylene.

4. Aromatic thioethers having the formula,

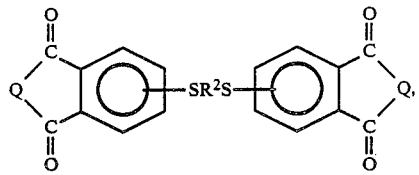

where $R^2$ is a $C_{(1-10)}$ divalent alkylene radical, and Q is a member selected from the class consisting of —O— and =$NR^1$, and $R^1$ is a $C_{(1-14)}$ monovalent organo radical.

5. Aromatic dianhydrides having the formula,

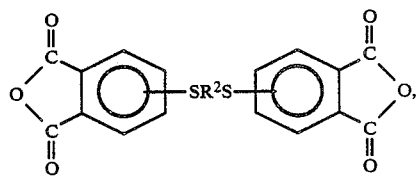

where $R^2$ is a $C_{(1-10)}$ divalent alkylene radical.

6. An aromatic dianhydride in accordance with claim 5, where $R^2$ is dimethylene.

7. An aromatic dianhydride in accordance with claim 5, where $R^2$ is trimethylene.

8. An aromatic dianhydride in accordance with claim 5, where $R^2$ is tetramethylene.

9. Method for making bis(thioetherimide)s of the formula,

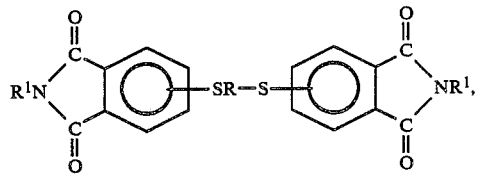

which comprises effecting reaction between a phthalimidothiolate having the formula,

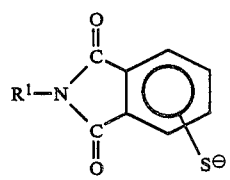

and organic dihalide of the formula,

XRX, where R is a $C_{(2-10)}$ divalent organo radical, and $R^1$ is a $C_{(1-14)}$ monovalent organo radical.

10. A method for making bisthioetherimides having the formula,

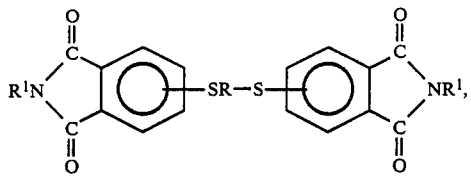

which comprises (1) effecting reaction between a halophthalimide having the formula,

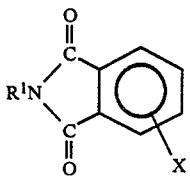

and an alkali metal sulfide having the formula, $M_2S$, to form organophthalimidothiolate of the formula,

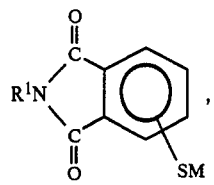

and (2) reacting the organophthalimidothiolate with organic dihalide of the formula,

XRX, where R is a $C_{(2-20)}$ divalent organo radical, $R^1$ is a $C_{(1-14)}$ monovalent organo radical, X is a halogen radical, and M is an alkali metal ion.

* * * * *